United States Patent
Greeley

(10) Patent No.: US 9,011,445 B2
(45) Date of Patent: Apr. 21, 2015

(54) RONGEUR AND METHOD FOR STIFFENING, GRASPING AND REMOVING TISSUE FROM A REGION OF THE SPINE

(71) Applicant: Roger D. Greeley, Portsmouth, NH (US)

(72) Inventor: Roger D. Greeley, Portsmouth, NH (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 136 days.

(21) Appl. No.: 13/793,924

(22) Filed: Mar. 11, 2013

(65) Prior Publication Data

US 2014/0257301 A1 Sep. 11, 2014

(51) Int. Cl.
*A61B 17/16* (2006.01)
*A61B 18/18* (2006.01)
*A61B 18/14* (2006.01)
*A61B 18/00* (2006.01)

(52) U.S. Cl.
CPC ......... *A61B 17/1606* (2013.01); *A61B 18/1445* (2013.01); *A61B 2018/00339* (2013.01); *A61B 2218/002* (2013.01)

(58) Field of Classification Search
USPC ................................................ 606/50, 51, 83
See application file for complete search history.

(56) References Cited

U.S. PATENT DOCUMENTS

| | | | |
|---|---|---|---|
| 5,766,177 A | 6/1998 | Lucas-Dean et al. | |
| 6,073,051 A | 6/2000 | Sharkey et al. | |
| 6,200,320 B1 | 3/2001 | Michelson | |
| 6,264,650 B1 | 7/2001 | Hovda et al. | |
| 6,620,155 B2 | 9/2003 | Underwood et al. | |
| 7,108,696 B2 | 9/2006 | Daniel et al. | |
| 7,204,851 B2 | 4/2007 | Trieu et al. | |
| 7,270,658 B2 | 9/2007 | Woloszko et al. | |
| 7,270,659 B2 | 9/2007 | Ricart et al. | |
| 7,393,351 B2 | 7/2008 | Woloszko et al. | |
| 7,794,456 B2 | 9/2010 | Sharps et al. | |
| 7,877,852 B2 | 2/2011 | Unger et al. | |
| 8,123,750 B2 | 2/2012 | Norton et al. | |
| 8,192,432 B2 | 6/2012 | McGaffigan | |
| 8,211,105 B2 | 7/2012 | Buysse et al. | |
| 2005/0090816 A1 | 4/2005 | McClurken et al. | |
| 2007/0260235 A1* | 11/2007 | Podhajsky | 606/41 |
| 2010/0087816 A1* | 4/2010 | Roy | 606/48 |

* cited by examiner

Primary Examiner — Christopher Beccia
(74) Attorney, Agent, or Firm — Jeffrey J. Hohenshell

(57) ABSTRACT

Rongeur and method for removing intervertebral disk tissue from a spinal column of a patient. A pair of bipolar electrodes on an elongated shaft is placed in proximity to the intervertebral disk tissue. Without withdrawing the instrument from the spinal column, the electrodes are activated with a source of RF energy to stiffen the intervertebral disk tissue, a source of saline solution is supplied to the intervertebral disk tissue and the intervertebral disk tissue is grasped with a grasping tool affixed in conjunction with the distal portion of the elongated shaft biting off a portion of the intervertebral disk tissue having been stiffened. The instrument is withdrawn from the spinal column of the patient to remove the portion of the intervertebral disk tissue. The inserting step, the placing, activating, supplying, grasping, and withdrawing steps are repeated until a desired portion of the intervertebral disk tissue has been removed.

20 Claims, 13 Drawing Sheets

RONGEUR AND METHOD FOR STIFFENING, GRASPING AND REMOVING TISSUE FROM A REGION OF THE SPINE

FIELD

The present invention relates generally to rongeurs and, more particularly, to rongeurs and methods for removing tissue from a region of the spine of a patient.

BACKGROUND

It is well known to use rongeurs to remove tissue, e.g., nucleus pulposus, from a region of the spine. For example, U.S. Pat. No. 6,200,320, Michelson, discloses a multi-bite bone cutting rongeur with an ultrathin foot plate and a disposable cutting element and storage chamber unit. Rongeurs are surgical instruments for the cutting away of human tissue, and most commonly, cartilage and/or bone. Rongeurs are known to be used in the spinal canal and about delicate neural structures.

A rongeur with an elongated shaft may be inserted into the intervertebral space of a patient. Jaws on the end of the rongeur may be closed around a portion of the tissue to be removed, a portion of the material may be bitten off by the jaws of the rongeur and the rongeur may be removed from the intervertebral space removing the portion of the material held between the jaws of the rongeur.

This procedure works reasonably well except that the tissue, e.g., nucleus pulposus, has a tendency to break into relatively small pieces when grasped by the jaws of the rongeur. Hence, only a relatively small piece of the tissue may be removed with reach insertion of the rongeur into the intervertebral space and subsequent removal.

Electrosurgical instruments have been used to either cut, e.g., Bovie-style cutting, or to transcollate, coagulate tissue and staunch blood flow.

Some devices have combined a grasping device and the use of electrical energy. For example, U.S. Pat. No. 8,192,432, McGaffigan, discloses a tissue cutting and sealing device, having a pair of opposing elements dimensioned to grasp tissue therebetween and a heating assembly on at least one of the opposing elements. The electrical energy is utilized to heat an object, at least one of the opposing jaws, to seal a vessel.

U.S. Pat. No. 8,211,105, Buysse et al, discloses an electrode assembly for use in combination with an electrosurgical instrument having opposing end effectors and a handle for effecting movement of the end effectors relative to one another. The electrosurgical instrument has a pair of electrodes each having an electrically conductive sealing surface and an insulating substrate. The electrosurgical instrument is used to both mechanically clamp and uses electrical energy to effect hemostasis by heating the tissue and blood vessels to coagulate, cauterize and/or seal tissue.

U.S. Pat. No. 6,073,051, Sharkey et al, discloses an externally guided intervertebral disc apparatus which manipulates tissue at a selected location of an intervertebral disc. In addition to having a distal section with sufficient flexibility to be compliant to the inner wall of the annulus fibrosus but insufficient penetration ability to be advanceable out through the annulus fibrosus, the apparatus transmits electromagnetic energy in order to provide advantageous, controllable heating (without charring or vaporizing).

SUMMARY

A bipolar pituitary rongeur has been developed to aid in the removal of tissue from a region of the spine, e.g., nucleus pulposus. The rongeur can engage tissue and remove such tissue on a bite by bite basis. The rongeur is inserted into the region of the spine, tissue is gasped by jaws on the rongeur and a portion of the tissue is bitten off. The rongeur is then removed and the material (tissue) that has been grasped is removed as well. The rongeur is then re-inserted into the area of the spine, more tissue grasped, bitten off and removed. This process is typically repeated until a sufficient or desired amount of the tissue has been removed.

The amount of material in each "bite" will determine how many times the rongeur is inserted, new bites taken and removed before the sufficient or desired amount of tissue removal is achieved. With smaller "bites", a greater number of insertions is increased before the same of amount of material is removed. A greater number of insertions may result in increased costs and may result in increased risk to the patient, e.g., from prolonged anesthetic and a risk of infection upon each insertion.

Bipolar radio frequency (RF) energy is applied to the grasping jaws of the rongeur, not for the purpose of sealing or coagulating tissue as in the prior art, but across the tissue with a bipolar electrode on each jaw along with the application of saline to the tissue. This combination of treatment tends to stiffen the tissue, e.g., nucleus pulposus, with the effect that grasping stiffened (treated) tissue enables the jaws of the rongeur to bite off a larger chunk or piece or portion of the tissue than was typical without such treatment. With a larger "bite", more tissue may be removed with fewer separate insertions enabling a faster, more efficient and, potentially, safer removal of tissue from region of the spine than was otherwise possible. Without the combination of bipolar tissue-stiffening RF energy and saline in combination with grasping jaws on the rongeur, a minimum of double the number of insertions would be required to remove the same amount of tissue. The lack of stiffening of the material would further increase the number of insertions.

In an embodiment, a rongeur for grasping and removing tissue from a region of a spine of a patient having intervertebral disc tissue has an elongated shaft configured for navigation into an intervertebral disc. A lumen extends from the proximal portion to the distal portion of the elongated shaft. A pair of bipolar electrodes is physically coupled to the distal portion of the elongated shaft in proximity of the intervertebral disc tissue of the patient. A source of RF energy is selectively and operatively coupled to the pair of bipolar electrodes, the rongeur being configured to apply the RF energy to the intervertebral disc tissue of the patient. A grasping tool is affixed in conjunction with the distal portion of the elongated shaft. The grasping tool is configured to be placed in proximity of the intervertebral disc tissue of the patient when in an open position and is configured to grasp the intervertebral disc tissue of the patient when in a closed position. A connector is configured to fluidly couple a source of saline solution with the lumen. A handle is operatively coupled to the proximal portion of the elongated shaft and operatively coupled to the gasping tool configured to operate the grasping between the open position and the closed position.

In an embodiment, the RF energy is applied to the intervertebral disc tissue is sufficient to stiffen the intervertebral disc tissue.

In an embodiment, the grasping tool has a pair of mating jaws pivotably movable from the open position to the closed position.

In an embodiment, the handle is further configured to selectively activate the RF energy to the pair of bipolar electrodes.

In an embodiment, the handle is further configured to selectively facilitate a flow of the saline solution through the lumen to the proximity of the intervertebral disc tissue of the patient in conjunction with activation of the pair of bipolar electrodes with the RF energy.

In an embodiment, the RF energy has a power level of not more than thirty (30) watts.

In an embodiment, each of the pair of mating jaws have a usable surface area able to grasp the intervertebral disc tissue of the patient and wherein the usable surface area for each of the pair of mating jaws is approximately equal.

In an embodiment, the elongated shaft has an electrically insulated external surface.

In an embodiment, the elongated shaft is constructed of a ceramic material.

In an embodiment, a source of saline solution is fluidly coupled to the connector.

In an embodiment, a method removes intervertebral disk tissue from a spinal column of a patient. A distal portion of an elongated shaft of a surgical instrument is inserted into the spinal column of the patient. A pair of bipolar electrodes physically coupled to the distal portion of the elongated shaft of the surgical instrument is placed in proximity to the intervertebral disk tissue, such as the nucleus pulposus. Without withdrawing the distal portion of the surgical instrument from the spinal column of the patient, the pair of bipolar electrodes of the surgical instrument is activated with a source of RF energy to stiffen, e.g., to break cross links within the collagen molecule causing the tissue to become more associated with itself and strengthen, the intervertebral disk tissue. Without withdrawing the distal portion of the surgical instrument from the spinal column of the patient, a source of saline solution is supplied to the intervertebral disk tissue via the elongated shaft of the surgical instrument. Without withdrawing the distal portion of the surgical instrument from the spinal column of the patient, the intervertebral disk tissue is grasped with a grasping tool affixed in conjunction with the distal portion of the elongated shaft of the surgical instrument biting off a portion of the intervertebral disk tissue having been stiffened. The surgical instrument is withdrawn from the spinal column of the patient to remove the portion of the intervertebral disk tissue. The inserting step, the placing step, the activating step, the supplying step, the grasping step, and the withdrawing step are repeated until a desired portion of the intervertebral disk tissue has been removed from the spine of the patient.

In an embodiment, the grasping step is accomplished with a pair of mating jaws pivotably movable from an open position to a closed position.

In an embodiment, the activating step and the supplying at least partially overlap in time.

In an embodiment, the activating step is accomplished through control from a handle affixed in conjunction with a proximal portion of the elongated shaft of the surgical instrument.

In an embodiment, the supplying step is accomplished through control from the handle affixed in conjunction with a proximal portion of the elongated shaft of the surgical instrument.

In an embodiment, RF energy used in the activating step has a power level of not more than thirty (30) watts.

In an embodiment, each of the pair of mating jaws have a usable surface area able to grasp the tissue of the patient and wherein the usable surface area for each of the pair of mating jaws is approximately equal.

In an embodiment, the elongated shaft has an electrically insulated external surface.

In an embodiment, the elongated shaft is constructed of a ceramic material.

In an embodiment, the intervertebral disk tissue is nucleus pulposus.

FIGURES

DESCRIPTION

Figure 1:
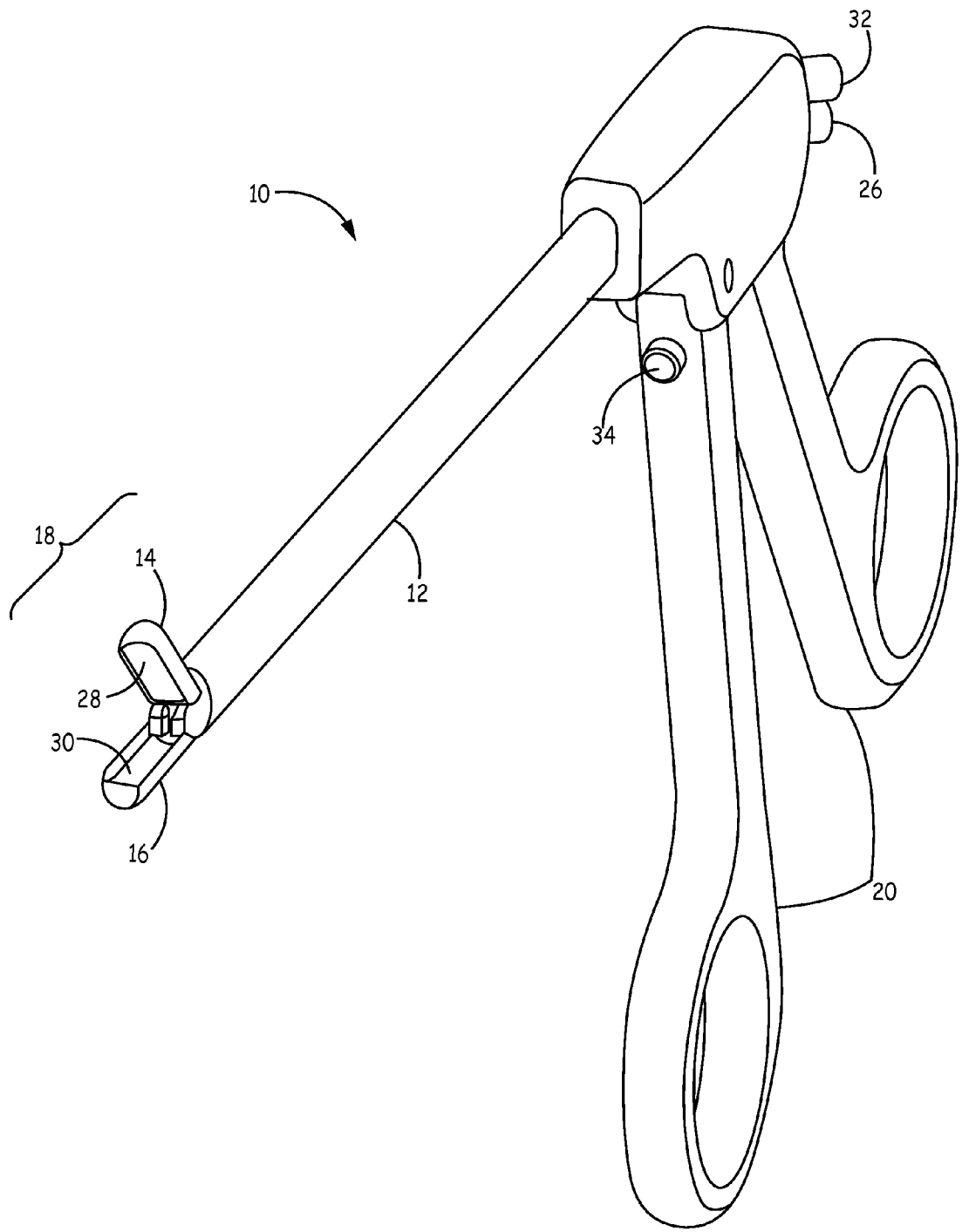
FIG. 1 is an isometric view of a rongeur.
Figure 6:
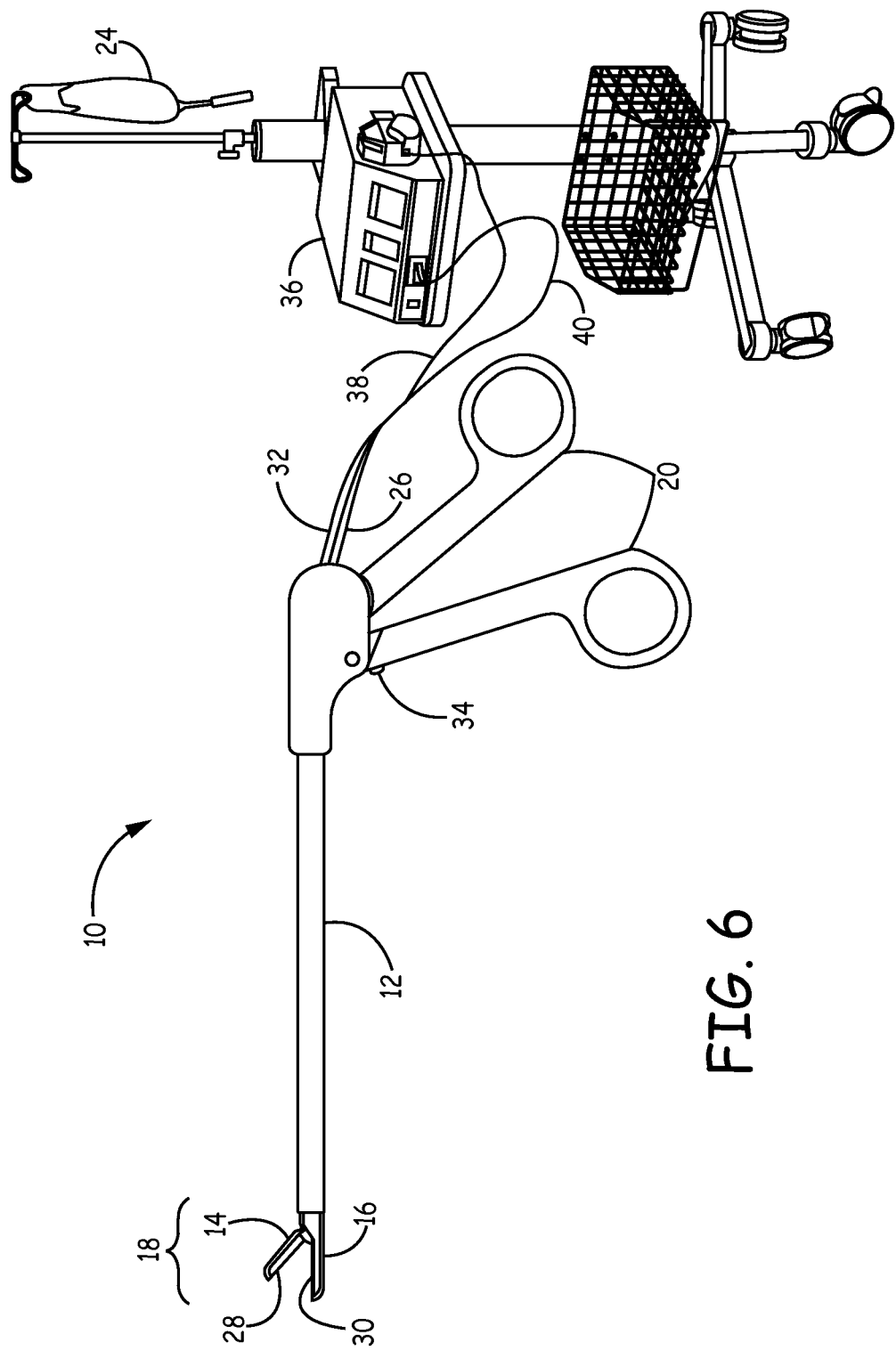
FIG. 6 illustrates the rongeur of FIG. 1 coupled to a source of RF energy and a source of saline.

As shown in FIG. 1, rongeur 10 has an elongated shaft 12 having opposing grasping upper jaw 14 and lower jaw 16 at distal end 18. Distal end 18 is configured to be placed in a region of the spine, for example, in the intervertebral space, for the grasping and subsequent removal of tissue, e.g., nucleus pulposus. Upper jaw 14 and lower jaw 16 may be operated by way of handle 20 near proximal end and configured to manipulate upper jaw 14 and lower jaw 16 between open (jaws apart) and closed (jaws relatively closer together or together) positions. As each portion of handle 20 is spread apart, upper jaw 14 and lower jaw 16 moves to a further apart, or open, position. As each portion of handle 20 is closed together, upper jaw 14 and lower jaw 16 moves closer together to a closed or near closed position. Elongated shaft 12 carries lumen 22 which is adapted to be coupled to a source of saline or saline solution 24 (FIG. 6). Connector 26 allows a fluid coupling between lumen 22 and the source of saline 24.

Bipolar electrodes 28, 30 positioned in upper jaw 14 and lower jaw 16, respectively, are electrically insulated from the outer surface of elongated shaft 12 and are electrically coupled to connector 32 that is configured to be coupled to a source of radio frequency (RF) energy 36. Trigger 34 is configured to initiate delivery of saline through lumen 22 to tissue of the region of the spine via distal end 18 and configured to apply RF energy 36 such tissue through bipolar electrodes 28, 30. While both RF energy 36 and saline 24 may be activated by a single trigger (as shown), it is to be recognized and understood that other activation mechanisms may be used including separate triggers on 20, one each for RF energy 36 and saline 24. Jaws 14, 16 are insulated from each other in a way such that electrodes 28, 30 are electrically separate to enable electrodes 28, 30 to pass energy between electrodes 28, 30 to treat the tissue. In an embodiment, the surface area of upper jaw 14 and lower jaw 16 are each approximately 52 millimeters$^2$ (per jaw). In an embodiment, the surface area of electrode 28 and electrode 30 are each approximately 116 millimeters$^2$ (per electrode).

Bipolar radio frequency (RF) energy is applied to the grasping jaws 14, 16 of rongeur 10, not for the purpose of sealing or coagulating tissue, but across the tissue with bipolar electrodes 28, 30 on each jaw 14, 16 along with the application of saline to the tissue. This combination of treatment tends to stiffen the tissue, e.g., nucleus pulposus, with the effect that grasping stiffened (treated) tissue enables the jaws of the rongeur to bite off a larger chunk or piece or portion of the tissue than was typical without such treatment. With a larger "bite", more tissue may be removed with fewer separate insertions enabling a faster, more efficient and, potentially, safer removal of tissue from region of the spine than was otherwise possible.

Figure 2:
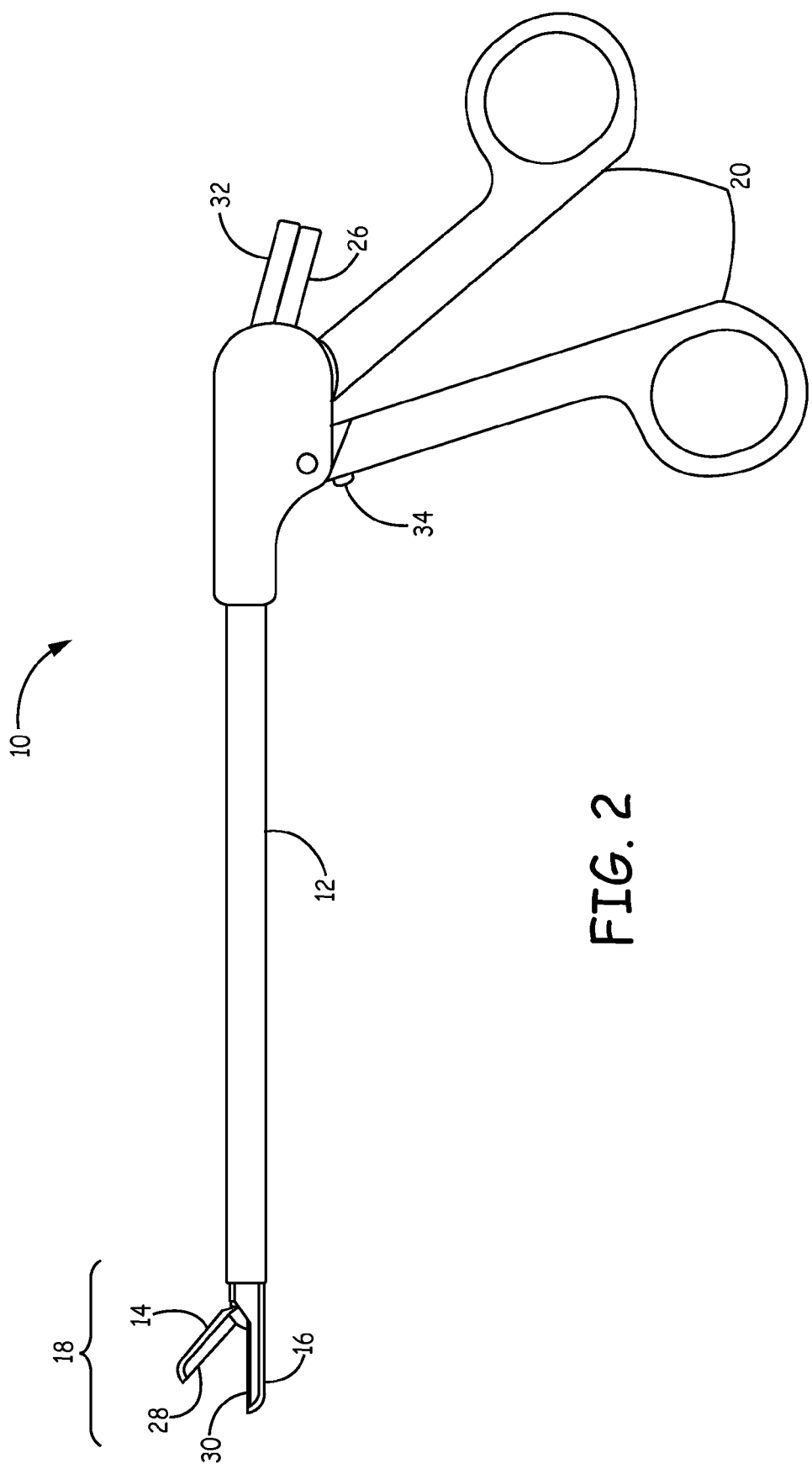
FIG. 2 is a side view of the rongeur of FIG. 1 with grasping jaws open.
Figure 3:
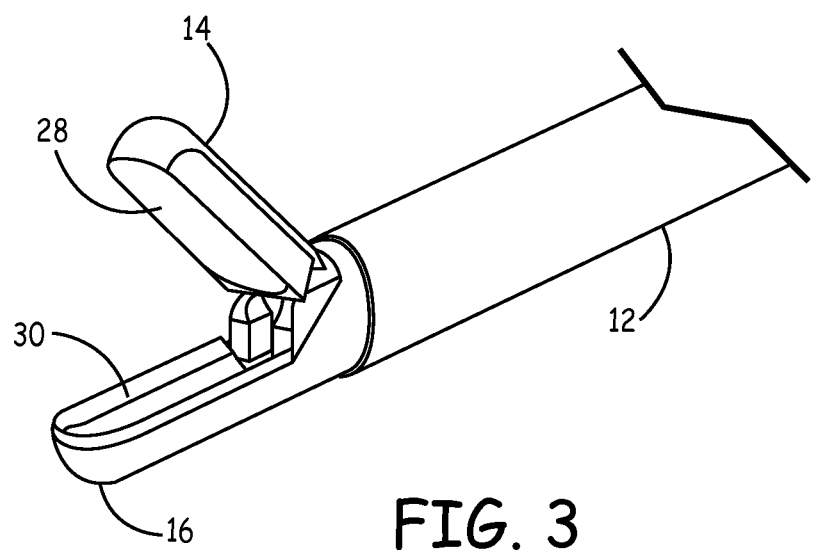
FIG. 3 is a close-up side view of the jaws portion of the rongeur of FIG. 2.

FIG. 2 and FIG. 3 illustrate rongeur 10 in side view with the portions of handle 20 spread relatively apart placing upper jaw 14 and lower jaw 16 in an open position. In the open position, distal end 18 of rongeur 10 may be placed in the proximity of the tissue to be removed.

Figure 4:
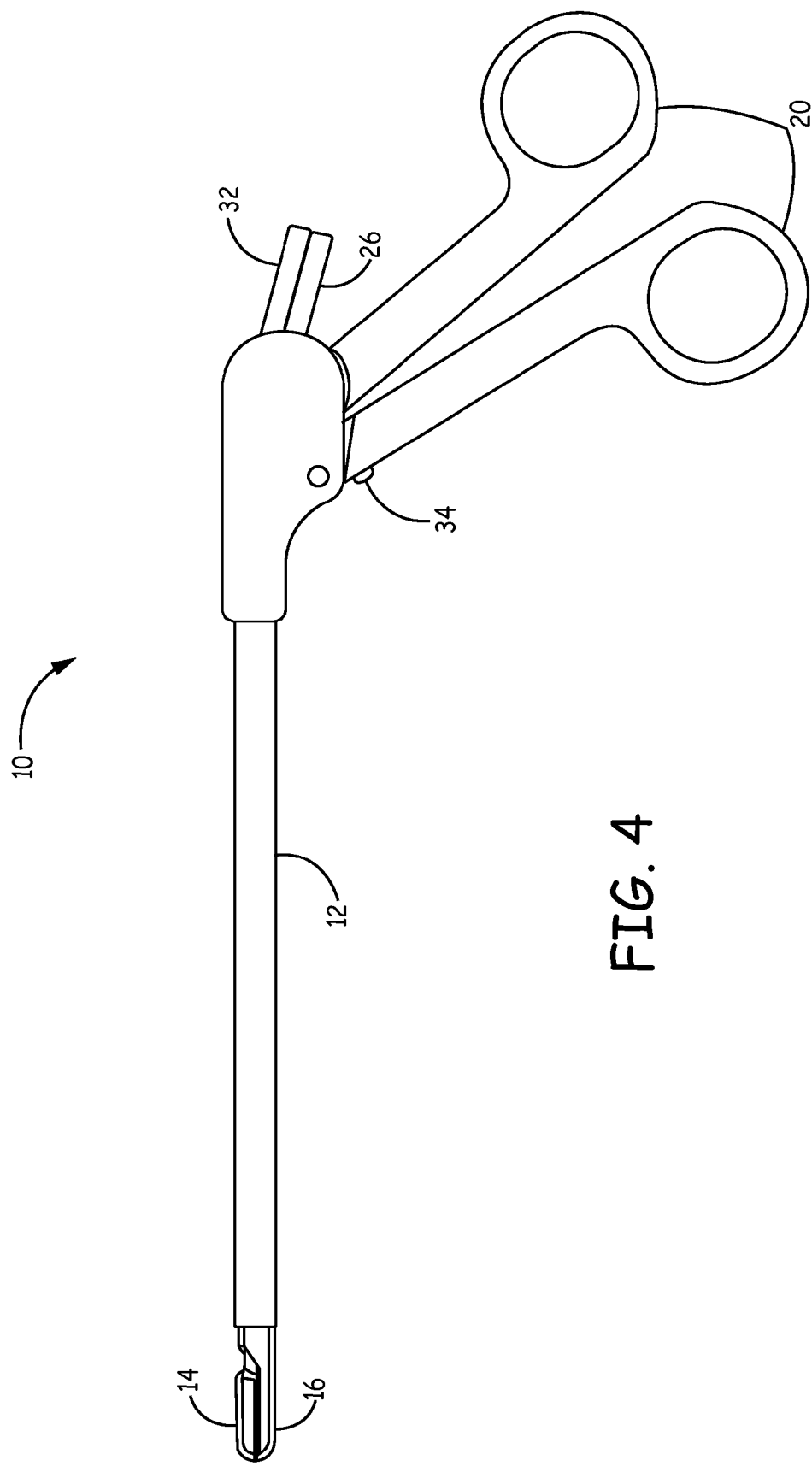
FIG. 4 is a side view of the rongeur of FIG. 1 with grasping jaws closed.
Figure 5:
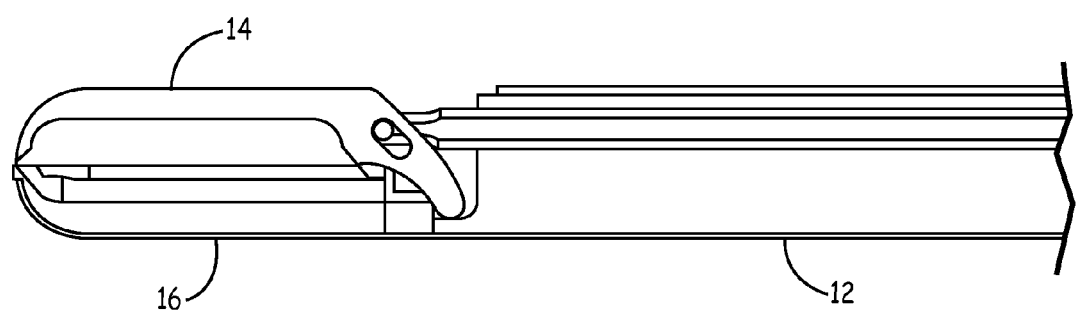
FIG. 5 is a close-up side view of the jaws portion of the rongeur of FIG. 4.

FIG. 4 and FIG. 5 illustrate rongeur 10 in side view with the portions of handle 20 spread relatively close together placing upper jaw 14 and lower jaw 16 in an closed position. In the closed position, distal end 18 of rongeur 10 may engage the tissue to be removed. RF energy and saline may be supplied to the tissue to treat the tissue for stiffening. With the tissue stiffened, grasping jaws 14, 16 will be able to "bite" off a larger chunk or portion of the tissue to be removed making the removal process more efficient.

FIG. 6 illustrates rongeur 10 electrically and fluidly coupled to source of saline 24 and source of RF energy 36. Saline connector 26 is fluidly coupled via tubing 38 to source of saline 24 allowing saline 24 to be supplied to the site at which tissue in a region of the spine is to be removed. RF connector 32 is electrically coupled to source of RF energy 36 via cables 40.

In an embodiment, an amount of RF energy 36 delivered to the tissue to be removed can be described as from 20 to 70 Watts delivered at a frequency of from 300 kiloHertz to 4 megaHertz in a time of from 0.5 to 5 seconds. General tissue and nucleus pulposus 54 are expected to react similarly.

Saline is provided from an outlet at or near the proximal end of upper jaw 14 and lower jaw 16 from tubing through elongated shaft 12 and connector 26 from saline source 24. Saline flow is provided either by gravity or a pump such as a peristaltic pump. In an embodiment, saline flow could also be provided through a pump/generator such as the Aquamantys™ system[1] that integrates both RF energy 36 and saline 24 flow. In general, the amount of saline delivered to the area of the tissue to be removed is a sufficient amount to generally wet the area and keep the tissue damp. The flow of saline 24 may be based on the power setting of RF energy 36 generator. Nominal flow rate at 20 Watts is approximately 2.58 milliliters/minute. At 70 Watts, the nominal flow rate is approximately 9.03 milliliters/minute. U.S. Patent Application Publication No. US 2005/0090816, McClurken et al, which is hereby incorporated by reference in its entirety, describes in general the relationship between power and saline flow.

[1] Aquamantis is a trademark of Medtronic, Inc., Minneapolis, Minn.

FIGS. 7 through 13 illustrate a step by step process in which rongeur 10 may be utilized to remove tissue in the region of the spine, in particular, the nucleus pulposus.

Figure 7:
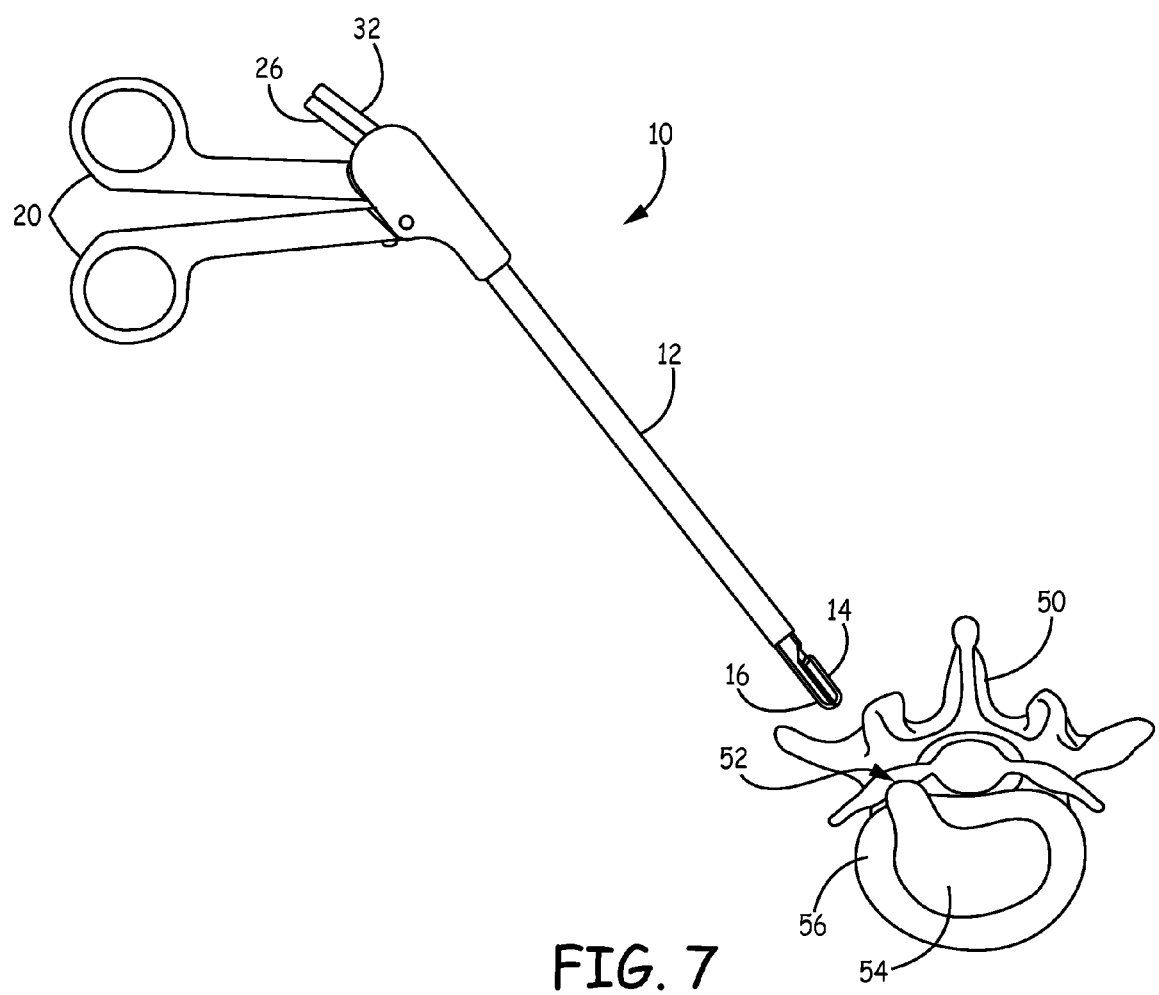
FIG. 7 illustrates the rongeur being brought to the region of the spine.

In FIG. 7 rongeur 10 is brought to the region of the spine. A typical herniated disc is shown with the nucleus pulposus breaking through the annulus fibrosis and creating pressure on the nerve. After access has been established, rongeur 10 is brought into the surgical site.

Figure 8:
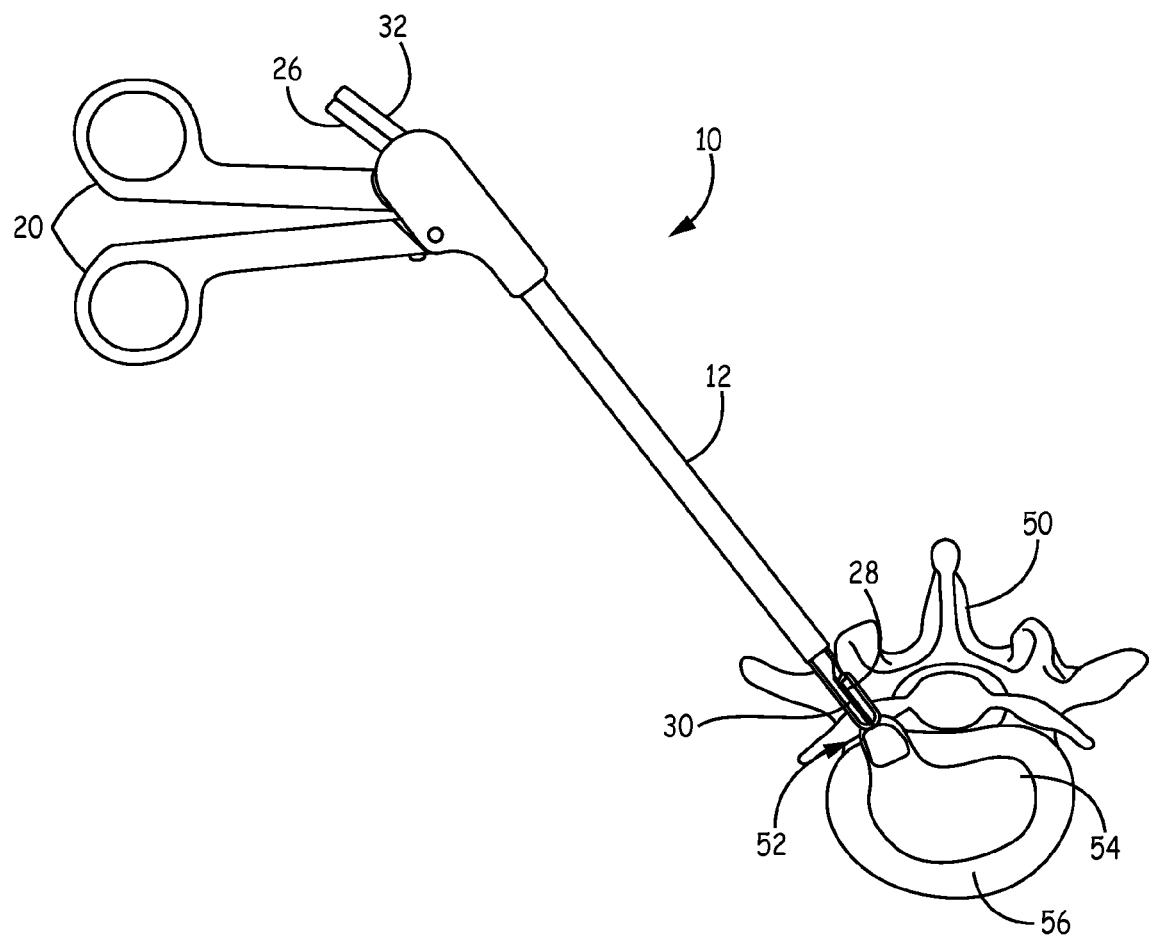
FIG. 8 illustrates the rongeur placed near the tissue to be removed and activation with RF energy and saline.

In FIG. 8 rongeur 10 is placed near the tissue to be removed. Rongeur 10 is activated using trigger 34 to deliver saline 24 to the tissue and supply RF energy 36 as discussed above to the tissue. Treatment with RF energy 36 and saline 24 causes a portion of the tissue to stiffen or solidify. RF energy 36 is supplied to the tissue to be removed to break cross links within the collagen molecule causing the tissue to become more associated with itself and strengthen. RF energy 36 may be applied through electrodes 28, 30 either with upper jaw 14 and lower jaw 16 open or closed. In an embodiment, RF energy 36 is applied with upper jaw 14 and lower jaw 16 having been placed around a portion of the tissue to be removed and at least partially closed thereon.

Figure 9:
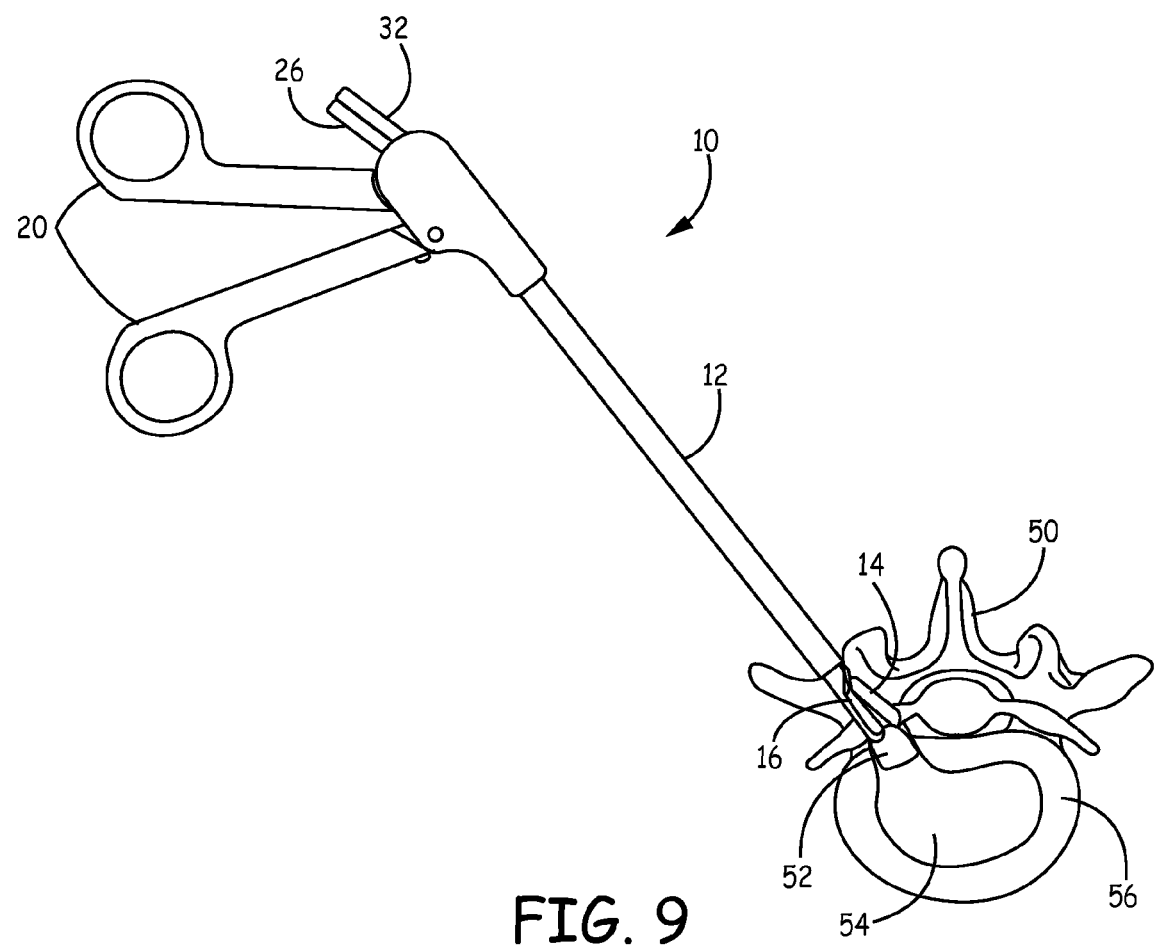
FIG. 9 illustrates the rongeur biting off at least a portion of the tissue to be removed.

In FIG. 9, without withdrawing rongeur 10 from the site, upper jaw 12 and lower jaw 14 close on, grasp, a portion of the tissue to be removed and rongeur 10 bites off at least a portion of the tissue to be removed.

Figure 10:
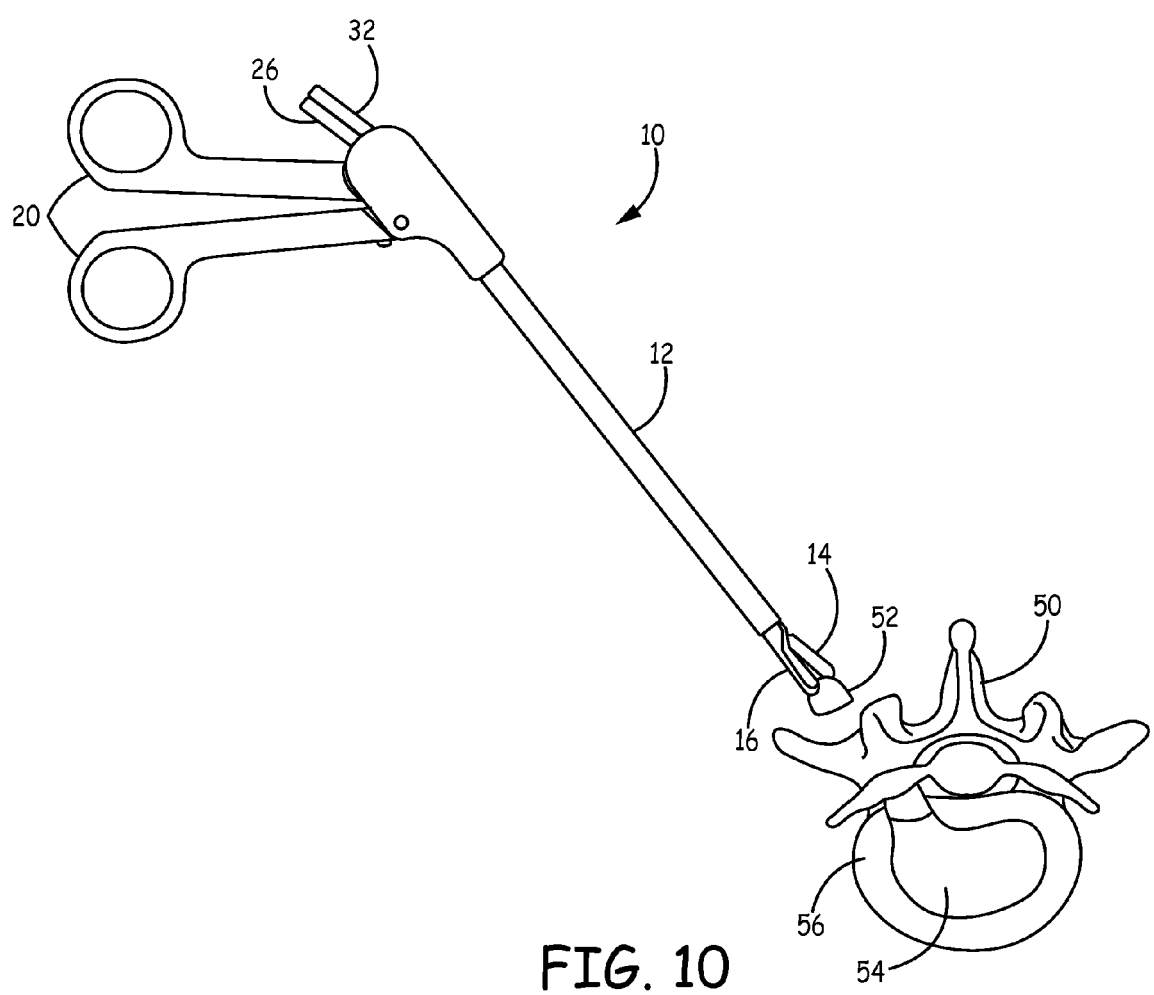
FIG. 10 illustrates the rongeur removing the tissue having been bitten off.

In FIG. 10 rongeur 10 is removed from the site having bitten off a portion of the tissue to be removed.

Figure 11:
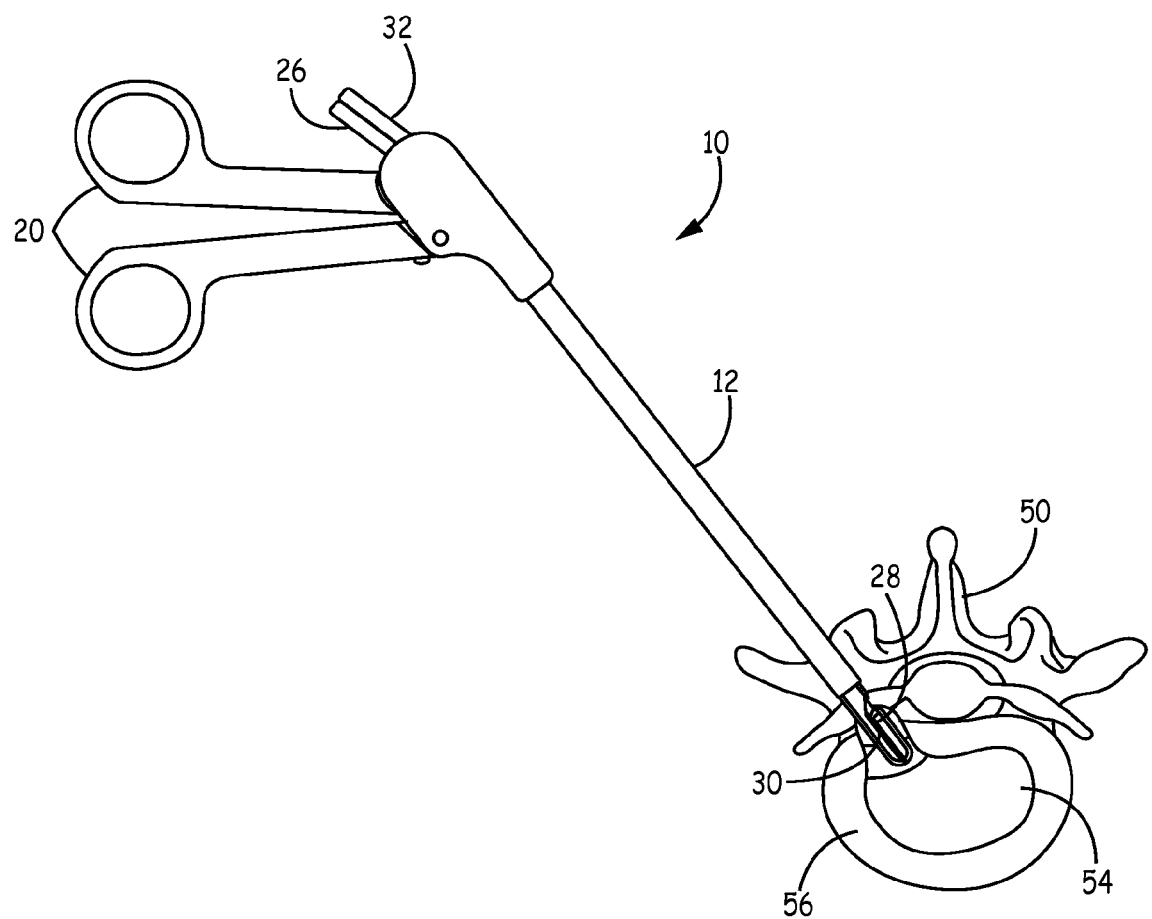
FIG. 11 illustrates the rongeur having been reinserted in the region of the spine and again activated with RF energy and saline to stiffen tissue to be removed.

In FIG. 11 rongeur 10 is reinserted in the region of the spine and again activated with RF energy 36 and saline 24 to stiffen the tissue the next section or portion of the material, tissue, to be removed.

Figure 12:
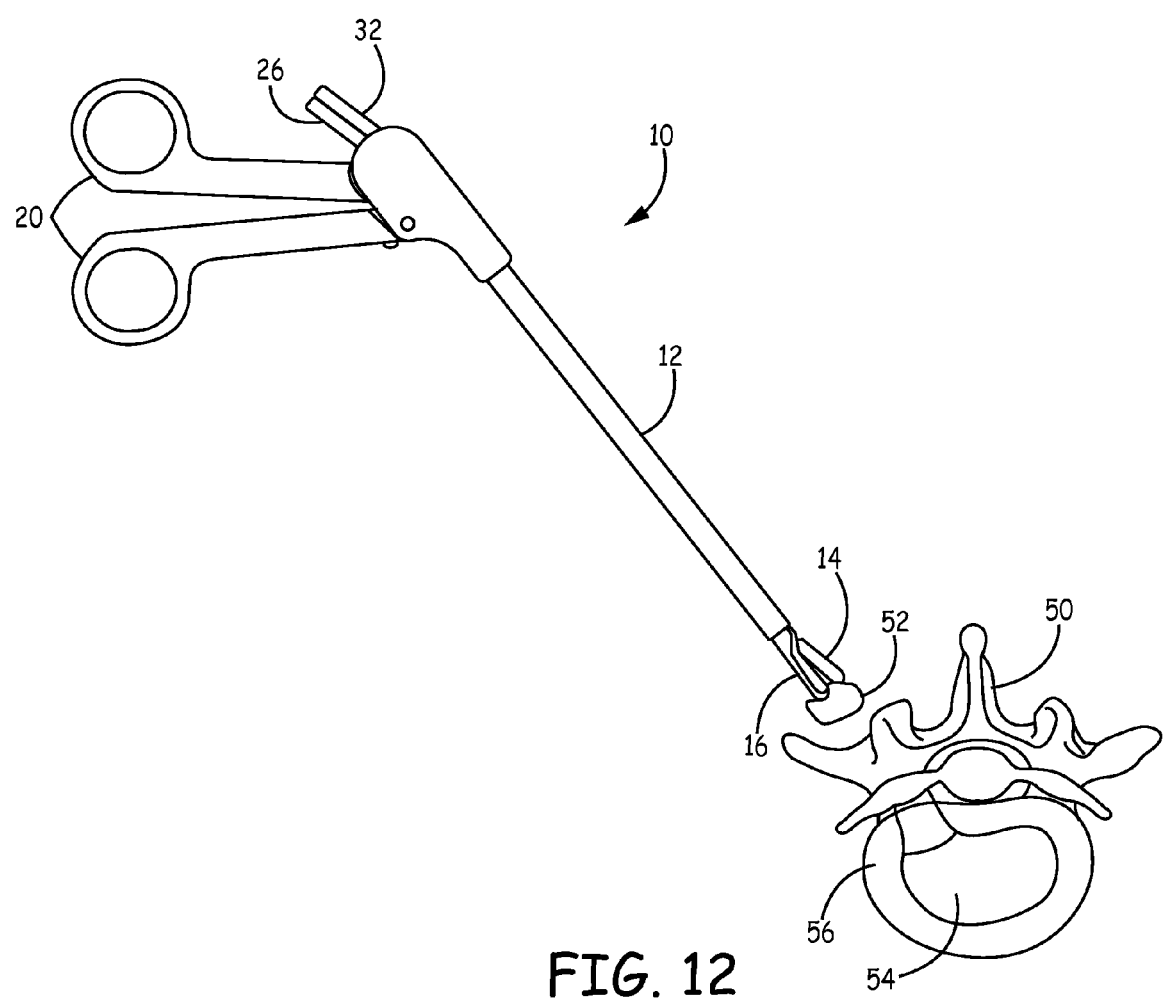
FIG. 12 illustrates the rongeur again removing tissue having been bitten off following stiffening.
Figure 13:
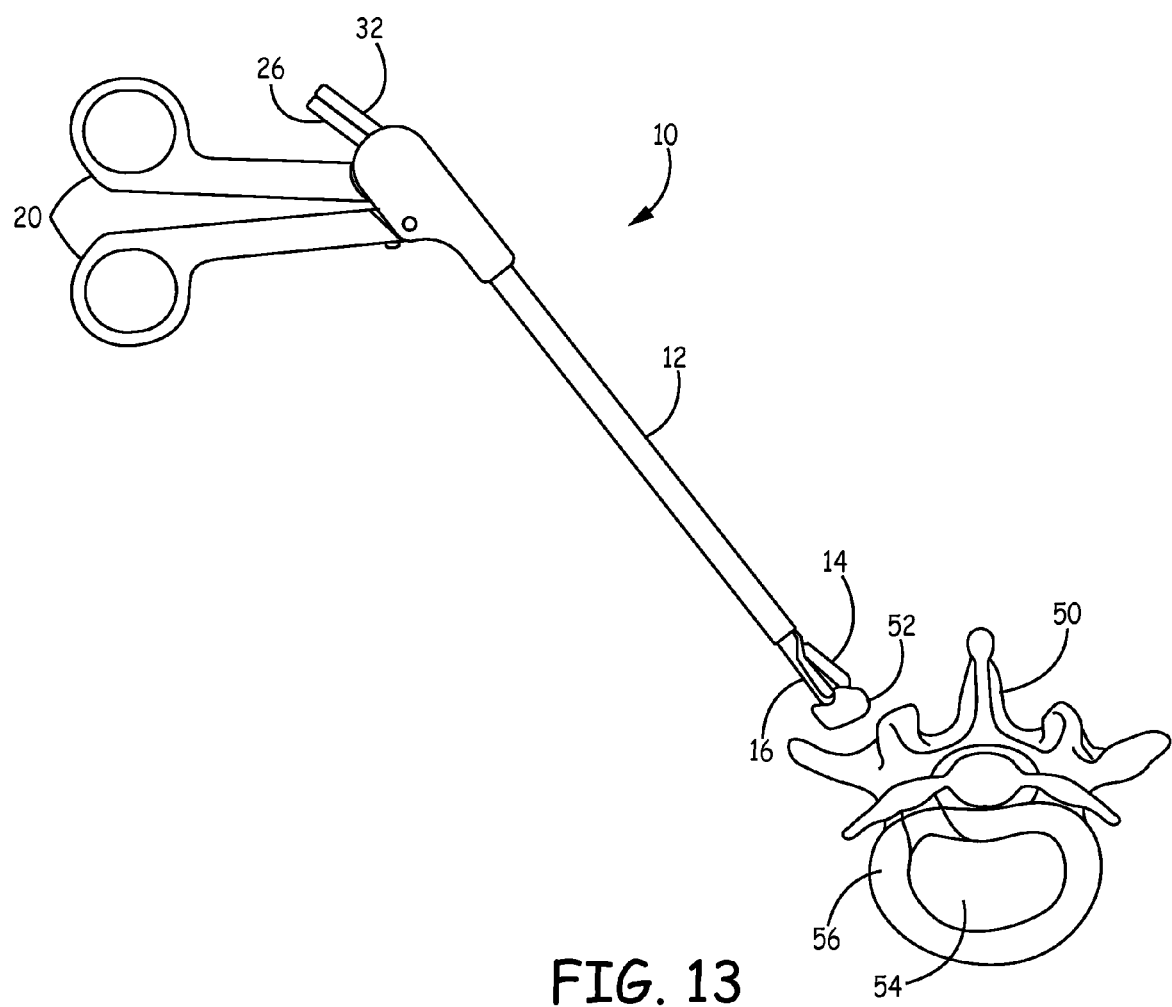
FIG. 13 illustrates the process being repeated.

FIG. 12 illustrates rongeur 10 again removing tissue that has been bitten off following the stiffening treatment illustrated in FIG. 11.

The process is repeated, inserting, treatment, grasping, biting off and removal (FIG. 13) until all of the nucleus pulposus is removed or until a sufficient amount or desired amount of the nucleus pulposus has been removed.

With the combination of stiffening treatment and grasping and removal of the tissue, e.g., nucleus pulposus, in a single instrument with the treated material enabling jaws 12, 14 to grasp and bite off a larger chunk or piece or portion of the tissue than was typical without such treatment, the process of removing tissue from the region of the spine has been made more efficient, faster and safer for the patient. With a larger "bite", more tissue may be removed with fewer separate insertions enabling a faster, more efficient and, potentially, safer removal of tissue from region of the spine than was otherwise possible.

Thus, embodiments of the rongeur and method for stiffening, grasping and removing tissue from a region of the spine are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A rongeur for grasping and removing tissue from a region of a spine of a patient having intervertebral disc tissue comprising:

an elongated shaft having a proximal portion and a distal portion, said elongated shaft having a lumen extending from said proximal portion to said distal portion, said elongated shaft being configured for navigation into an intervertebral disc; and a pair of bipolar electrodes physically coupled to said distal portion of said elongated shaft in proximity of said intervertebral disc tissue of said patient;

a source of RF energy selectively and operatively coupled to said pair of bipolar electrodes, said surgical instrument being configured to apply said RF energy to said intervertebral disc tissue of said patient;

a grasping tool affixed in conjunction with said distal portion of said elongated shaft, said grasping tool having an open position and a closed position, said grasping tool being configured to be placed in proximity of said intervertebral disc tissue of said patient when in said open position and being configured to grasp said intervertebral disc tissue of said patient when in said closed position;

a connector configured to fluidly couple a source of saline solution with said lumen; and a handle operatively coupled to said proximal portion of said elongated shaft and operatively coupled to said gasping tool configured to operate said grasping between said open position and said closed position.

2. The rongeur of claim 1 wherein said RF energy applied to said intervertebral disc tissue is sufficient to stiffen said intervertebral disc tissue.

3. The rongeur of claim 1 wherein said grasping tool comprises a pair of mating jaws pivotably movable from said open position to said closed position.

4. The rongeur of claim 1 wherein said handle is further configured to selectively activate said RF energy to said pair, of bipolar electrodes.

5. The rongeur of claim 4 wherein said handle is further configured to selectively facilitate a flow of said saline solution through said lumen to said proximity of said intervertebral disc tissue of said patient in conjunction with activation of said pair of bipolar electrodes with said RF energy.

6. The rongeur of claim 5 wherein said RF energy comprises a power level of not more than thirty (30) watts.

7. The rongeur of claim 4 wherein each of said pair of mating jaws have a usable surface area able to grasp said intervertebral disc tissue of said patient and wherein said usable surface area for each of said pair of mating jaws is approximately equal.

8. The rongeur of claim 1 wherein said elongated shaft has an electrically insulated external surface.

9. The rongeur of claim 8 wherein said elongated shaft comprises a ceramic material.

10. The rongeur of claim 1 further comprising a source of saline solution fluidly coo pled to said connector.

11. A method of removing intervertebral disk tissue from a spinal column of a patient, comprising;

inserting a distal portion of an elongated shaft of a surgical instrument to said spinal column of said patient;

placing pair of bipolar electrodes physically coupled to said distal portion of said elongated shaft of said surgical instrument in proximity to said intervertebral disk tissue;

without withdrawing said distal portion of said surgical instrument from said spinal column of said patient, activating said, pair of bipolar electrodes of said surgical instrument with a source of RF energy to stiffen said intervertebral disk tissue;

without withdrawing said distal portion of said surgical instrument from said spinal column of said patient, supplying a source of saline solution to said intervertebral disk tissue via said elongated shaft of said surgical instrument;

without withdrawing said distal portion of said surgical instrument from said spinal column of said patient, grasping said intervertebral disk tissue with a grasping tool affixed in conjunction with said distal portion of said elongated shaft of said surgical instrument to bite off a portion of said intervertebral disk tissue having been stiffened;

withdrawing said surgical instrument from said spinal column of said patient to remove said portion of said intervertebral disk tissue; and repeating said inserting step, said placing step, said activating step, said, supplying step, said grasping step, and said withdrawing step until a desired portion of said intervertebral disk tissue has, been removed from said spine of said patient.

12. The method of claim 11 wherein said grasping step is accomplished with a pair of mating jaws pivotably movable from an open position to a closed position.

13. The method of claim 12 wherein a said activating step and said supplying at least partially overlap in time.

14. The method of claim 13 wherein said activating step is accomplished through control from a handle affixed in conjunction with a proximal portion of said elongated shaft of said surgical instrument.

15. The method claim 14 wherein said supplying step is accomplished through control from said handle affixed in conjunction with a proximal portion of said elongated shaft of said surgical instrument.

16. The method of claim 15 wherein RF energy used in said activating step comprises a power level of not more than thirty (30) watts.

17. The method of claim 16 wherein each of said pair of mating jaws have a usable surface area able to grasp said tissue of said patient and wherein said usable surface area for each of said pair of mating jaws is approximately equal.

18. The method of claim 17 wherein said elongated shaft has an electrically insulated external surface.

19. The method of claim 18 wherein said elongated shaft comprises a ceramic material.

20. The method of claim 11 wherein said intervertebral disk tissue comprises nucleus pulposus.

* * * * *